(12) United States Patent
Dow et al.

(10) Patent No.: US 9,345,762 B2
(45) Date of Patent: May 24, 2016

(54) STAYED ROLLER FURLER

(71) Applicant: Hobie Cat Company, Oceanside, CA (US)

(72) Inventors: Philip James Dow, Oceanside, CA (US); Gregory Scott Ketterman, Oceanside, CA (US); James Taylor Czarnowski, Fallbrook, CA (US); Jason Christopher Kardas, Vista, CA (US)

(73) Assignee: Hobie Cat Company, Oceanside, CA (US)

( * ) Notice: Subject to any disclaimer, the term of this patent is extended or adjusted under 35 U.S.C. 154(b) by 0 days.

(21) Appl. No.: 14/546,339

(22) Filed: Nov. 18, 2014

(65) Prior Publication Data

US 2015/0175243 A1   Jun. 25, 2015

Related U.S. Application Data

(60) Provisional application No. 61/919,391, filed on Dec. 20, 2013.

(51) Int. Cl.

| | |
|---|---|
| *A61K 39/39* | (2006.01) |
| *B63H 9/08* | (2006.01) |
| *B63B 15/02* | (2006.01) |
| *A61K 39/395* | (2006.01) |
| *C07K 16/40* | (2006.01) |
| *B63B 1/12* | (2006.01) |
| *B63B 15/00* | (2006.01) |
| *A61K 39/00* | (2006.01) |

(52) U.S. Cl.
CPC .............. *A61K 39/39* (2013.01); *A61K 39/3955* (2013.01); *B63B 1/121* (2013.01); *B63B 15/02* (2013.01); *B63H 9/08* (2013.01); *C07K 16/40* (2013.01); *A61K 2039/505* (2013.01); *B63B 2001/123* (2013.01); *B63B 2015/005* (2013.01); *C07K 2317/34* (2013.01); *C07K 2317/76* (2013.01); *C07K 2317/92* (2013.01)

(58) Field of Classification Search
CPC .............. B63H 9/04; B63H 9/06; B63H 9/08; B63H 9/10; B63H 9/1021; B63H 9/1028; B63B 15/0083; B63B 15/02; B63B 35/73; B63B 1/10
USPC ........ 114/39.21, 39.26, 39.31, 39.32, 102.24, 114/104
See application file for complete search history.

(56) References Cited

U.S. PATENT DOCUMENTS

| | | | | |
|---|---|---|---|---|
| 4,230,060 | A | * 10/1980 | McCoy | .................. B63B 15/02 114/39.32 |
| 4,621,587 | A | * 11/1986 | Pool | ........................ B63B 35/71 114/39.32 |
| 2011/0048307 | A1 | * 3/2011 | Fernandez Puentes | .. B63H 9/08 114/39.32 |

*Primary Examiner* — Lars A Olson
(74) *Attorney, Agent, or Firm* — Joseph E. Mueth, Esq.

(57) ABSTRACT

A wind powered craft carrying a generally vertical mast which is rotatable about its vertical axis, having a sail carried by the mast with its bottom edge attached in proximity to the bottom of the mast and extending to an attachment point in proximity to the top of the mast. A generally horseshoe-shaped member having an open end is and extending around said mast. The mast being rotatable within the horseshoe-shaped member. A bearing supported stationary member at the top of the mast is carried by the mast while allowing the mast to rotate. A support stay runs from the horseshoe-shaped member to the bearing supported member to support the horseshoe-shaped member. Additional stays are attached to the horseshoe-shaped member and splayed to attach to opposed sides of the hull of the watercraft. The sail is reefed around the mast through the open end of the horseshoe-shaped member.

6 Claims, 6 Drawing Sheets

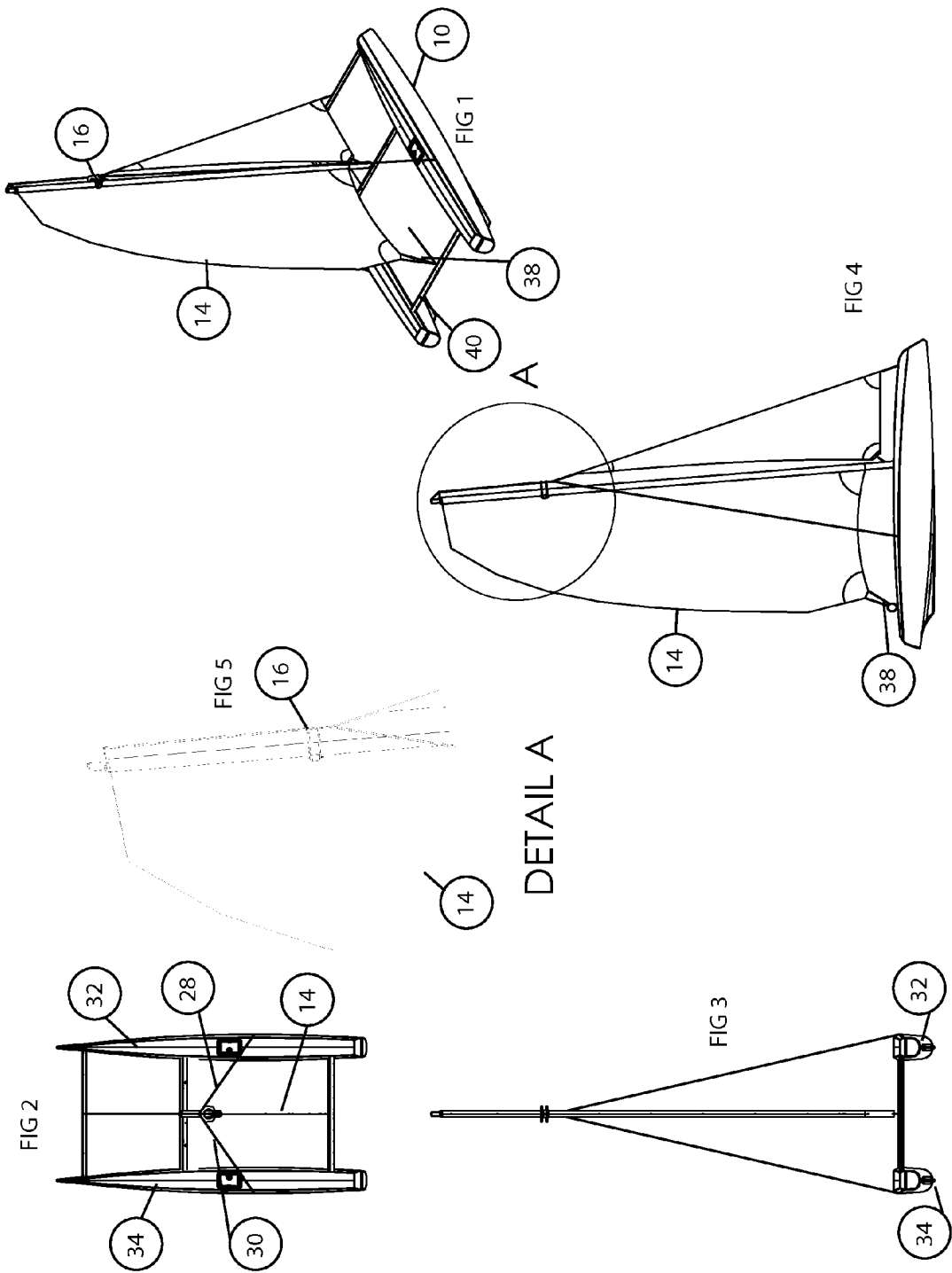

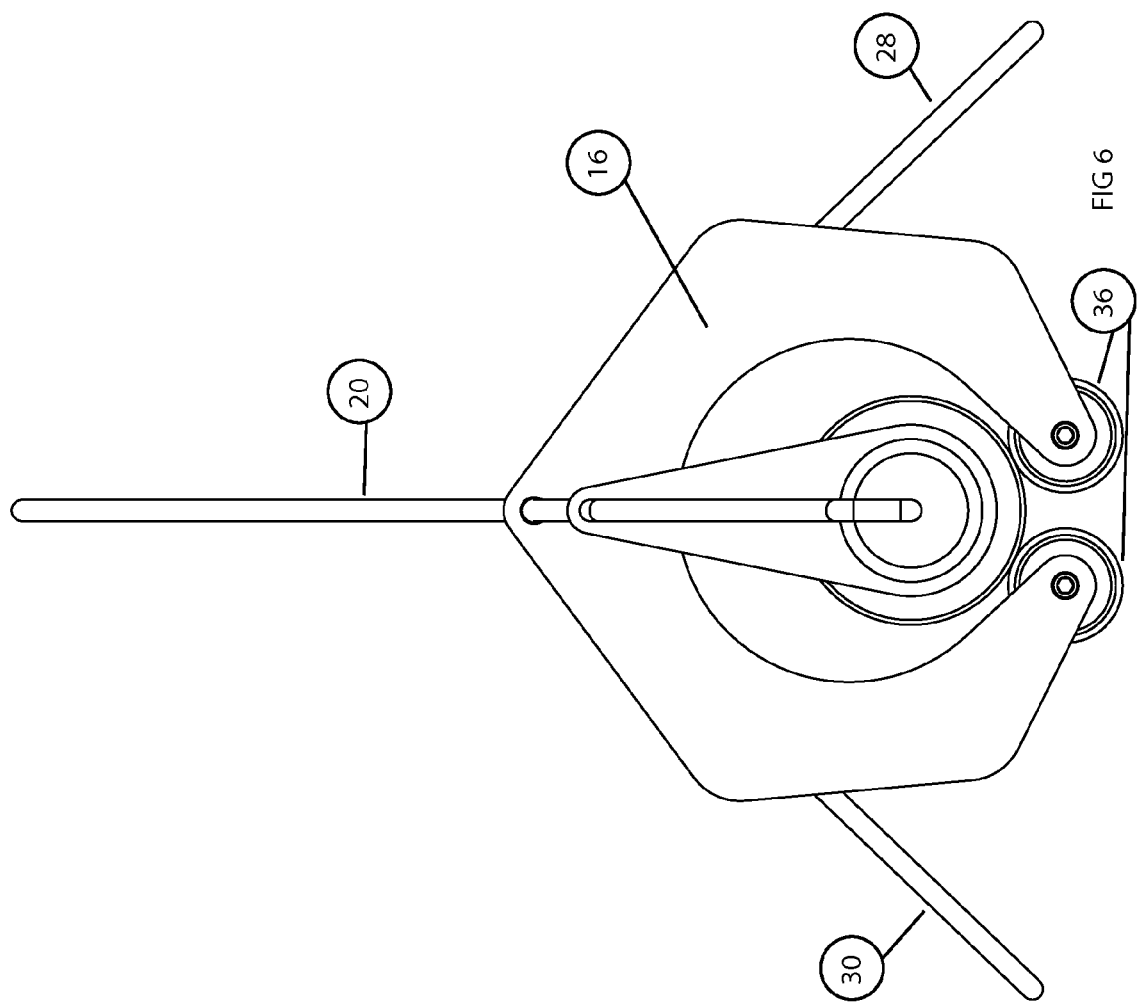

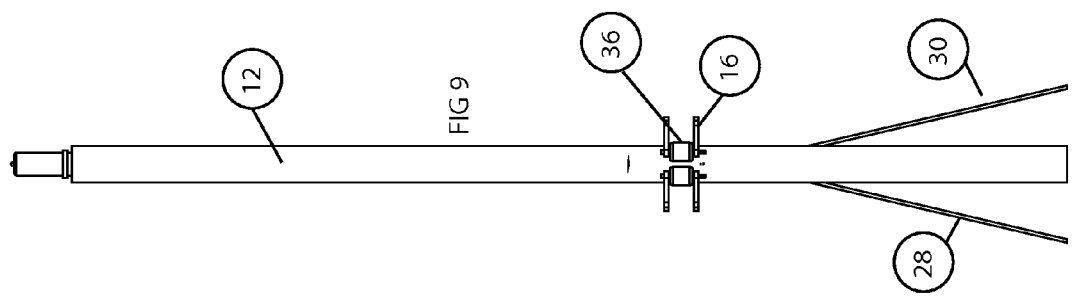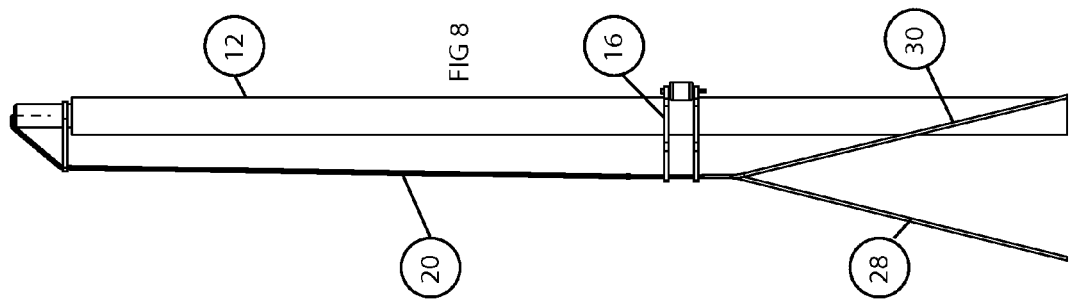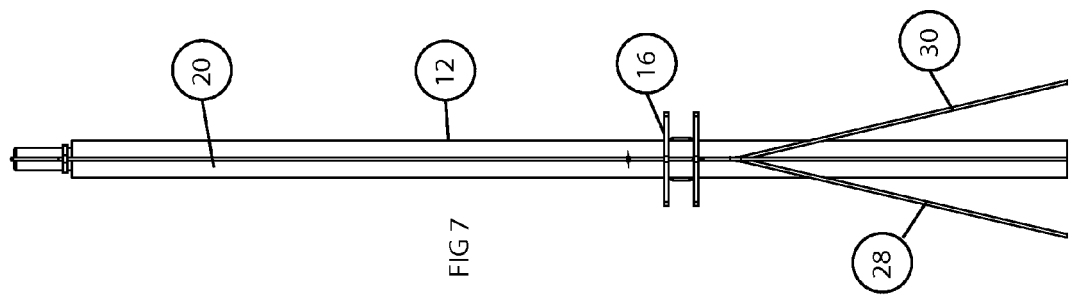

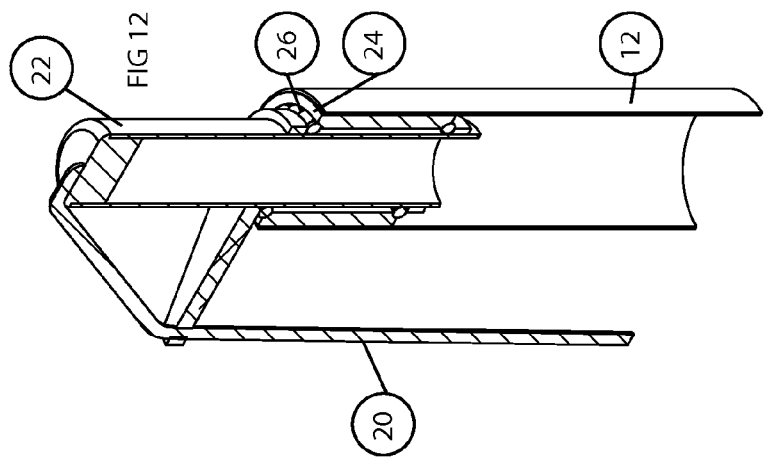
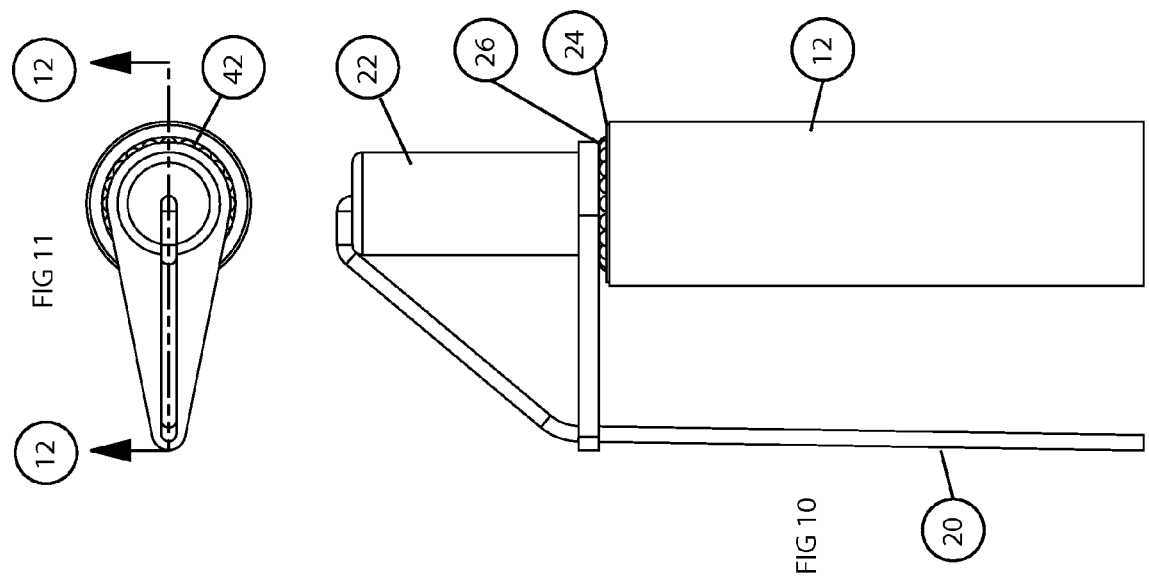

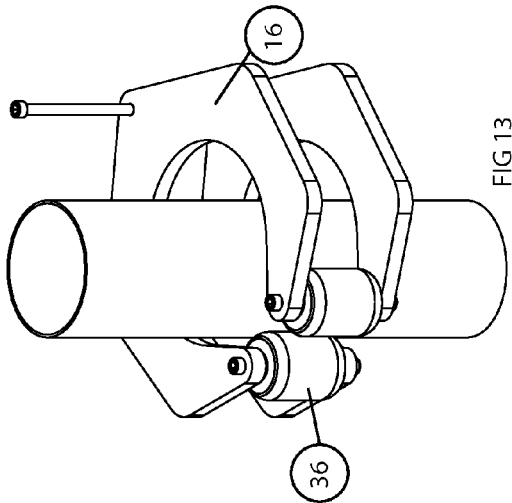
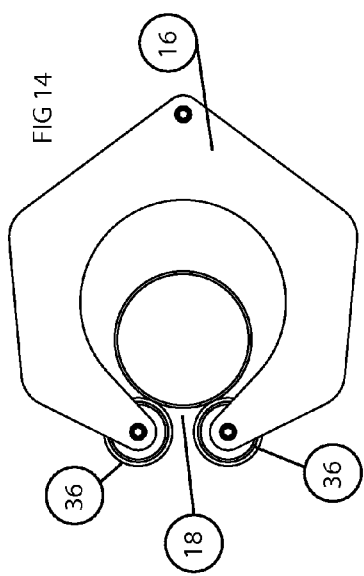
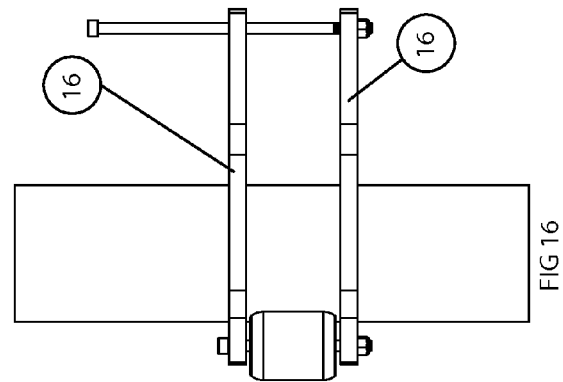
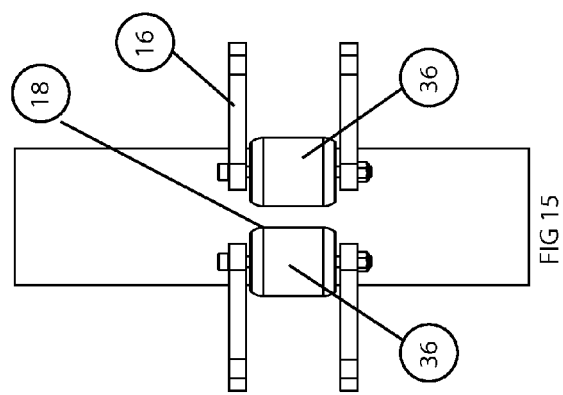

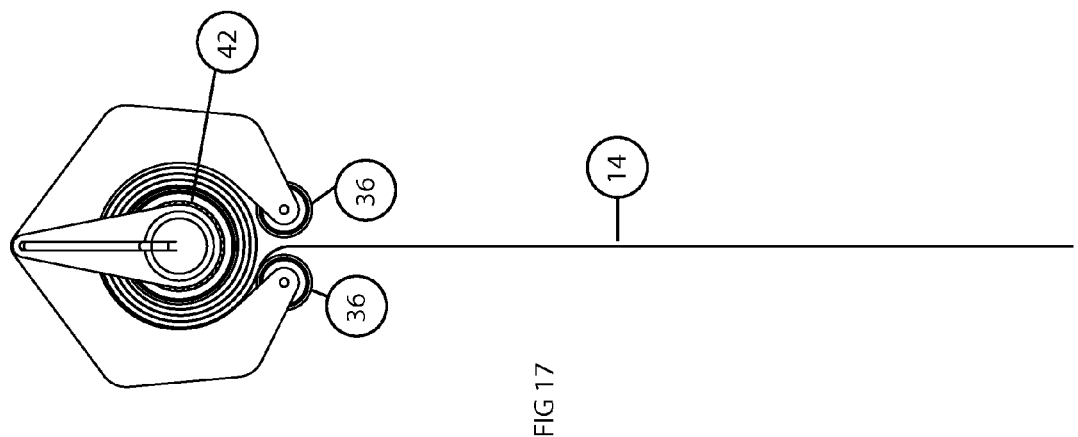

STAYED ROLLER FURLER

This patent application claims the benefit of the filing date of U.S. Provisional Patent Application Ser. No. 61/919,391, filed Dec. 20, 2013, the disclosure of which is incorporated herein by reference.

FIELD OF INVENTION

This invention relates to novel watercraft.

BACKGROUND OF INVENTION

Sailboats rely on harnessing the power of the wind to create propulsion. In its most basic form, this is accomplished by affixing a vertical mast to the boat with a sail attached to the length of the mast on one side, and to an adjustable rope on the opposite corner. To support the load on the mast, the mast is connected in a cantilever fashion to the hull. Most sail rigs include a compressive member attached to the lower end of the mast below the sail, extending horizontally to the opposite tip of the sail. This is referred to as a boom. To improve the aerodynamics of the sail, battens are often integrated into the sail cloth. Battens are most commonly constructed of fiberglass rods, and are oriented in a generally horizontal position, spaced out along the vertical length of the sail.

A variation on this conventional rig allows the mast to spin around its vertical axis. This is achieved by supporting a short length of the base of the mast with bearings. Spinning the mast consequently causes the sail to wrap, or furl around the diameter of the mast. This is a benefit to the functionality of the sailboat, allowing the user to furl or unfurl the sail to attain the appropriate amount of sail area for the conditions, or completely furl the sail. Furling the sail around the mast requires the sail to not have horizontal battens, as they are not flexible enough to wrap around the small diameter of the mast. Instead, diagonal battens are used. The compromise to this style of rig is that supporting the mast only at the base compromises the efficiency of the rig because the tip of the mast bends away under the load of the wind, decreasing the amount of power that can be harnessed. It also requires a very strong connection between the hull and the mast, and a stiff mast.

In an effort to increase strength and decrease weight, many sailboats use stays to transmit the load of the mast to the hull of the boat. Stays are the tension members. They are wires or ropes affixed to the mast approximately two-third to three-quarters up the length of the mast. Supporting the mast at this location allows for a balanced wind loading of the mast, minimizing bending and therefore keeping an optimized sail shape. These stays extend down to the left and right sides of the hull and the front of the hull. Using stays to support the mast allows the base of the mast to be simply supported on the hull. It also decreases the strength requirements of the supporting hardware due to the larger moment arm, decreasing the weight of the rig.

In high wind conditions, it can be necessary to decrease the amount of sail area to avoid overpowering or capsizing a sailboat. With a traditional stayed sail rig, the stays are affixed to the mast, precluding the sail from being furled around the mast because it cannot spin. The simplest solution to decreasing sail area with a stayed sail rig is called reefing. In this method, the sail is lowered part way down the length of the mast, and the lower section of the sail is gathered at the bottom of the sail. While this works, it is not very quick or tidy. Another design allows for a boom to spin as the sail is lowered down the length of the mast, furling the sail around the boom. A variation on this design works very similarly, but employs a rotating mandrel inside a hollow boom around which the sail wraps when furled. These two designs require a boom. Another design works in a similar fashion, but furls the sail around a mandrel inside the mast. This design precludes the use of battens and increases the weight of the mast. One more less common design allows for the sail to furl around the mast as it spins, with stays running to the tip of the mast. This is not a common design because only supporting the mast at the top and bottom creates a less optimal sail shape, as the mast bends in the middle. It also makes it difficult to spin the mast under sail load.

SUMMARY OF THE INVENTION

Briefly, the invention comprises a wind powered craft carrying a generally vertical mast supported by stays, said craft comprising means for supporting the mast with the stays along the vertical length of the mast but below the top of the mast while allowing the mast to rotate about its vertical axis.

The invention further comprises a wind powered craft carrying a generally vertical mast which is rotatable about its vertical axis, a sail carried by said mast with its bottom edge attached in proximity to the bottom of the mast and extending to an attachment point in proximity to the top of the mast, a first member having an open end and partially extending around said mast, the mast being rotatable within said member, a bearing mounted stationary second member at the top of the mast and carried by the mast while allowing the mast to rotate, a support stay running from said first member to said bearing mounted second member to support said first member, and additional stays attached to said first member and splayed to attach to opposed sides of the hull of the watercraft, said sail being reefed around said mast through the open end of said first member by rotation of the mast.

More particularly, the invention comprises a watercraft carrying a generally vertical mast which is rotatable about its vertical axis, a sail carried by said mast with its bottom edge attached in proximity to the bottom of the mast and extending to an attachment point in proximity to the top of the mast, a generally horseshoe-shaped member having an open end and partially extending around said mast, the mast being rotatable within the horseshoe-shaped member, a bearing mounted stationary member at the top of the mast and carried by the mast while allowing the mast to rotate, a support stay running from said horseshoe-shaped member to said bearing mounted member to support the horseshoe-shaped member, and additional stays attached to said horseshoe-shaped member and splayed to attach to opposed sides of the hull of the watercraft, said sail being reefed around said mast through the open end of said horseshoe-shaped member by rotation of the mast.

According to the present invention, the rig is properly supported by stays which still allow the sail to furl around the mast. To achieve this functionality, instead of attaching the stays directly to the mast, they are attached to a preferably horseshoe-shaped component which partially encompasses the mast in the same location approximately ⅔ to ¾ up the length of the mast, but is not attached to the mast. From this horseshoe, a support stay is run to the tip of the mast where it is affixed to a bearing, allowing the mast to rotate. This system allows for the vertical component of the force from the stays to be supported by the support stay leading to the tip of the mast, and the horizontal component of the force to be supported by the horseshoe. This device also allows the sail to furl around the mast, passing through the gap between the two ends of the horseshoe. To facilitate lower friction when furling and avoid damaging the sail cloth, rollers are attached to the ends of the horseshoe, allowing for the sail to feed through and wrap around the mast even when under load.

THE DRAWINGS

In the drawings:

FIG. 1 is a perspective view from the right rear of a catamaran equipped with the sail rig of the present invention.

FIG. 2 is a top view of a catamaran equipped with the sail rig of the present invention.

FIG. 3 is a rear view of a catamaran equipped with the sail rig of the present invention.

FIG. 4 is a side view of a catamaran equipped with the sail rig of the present invention.

FIG. 5 is an enlarged view of the top of the mast taken at A in FIG. 4.

FIG. 6 is an enlarged top view of the mast of the catamaran shown in FIGS. 1 to 4, showing in more detail the horseshoe-shaped member.

FIG. 7 is a front view of the mast carrying the horseshoe-shaped member and the first stay running from the horseshoe-shaped member to the top of the mast and the two splayed stays running to opposite sides of the catamaran.

FIG. 8 is a view of the mast of FIG. 7 taken from the side.

FIG. 9 is a rear view of the mast of FIG. 7.

FIG. 10 is a side view of the top of the mast showing the first stay and the bearing supported member carried at the top of the mast.

FIG. 11 is a top view of the top of the mast as shown in FIG. 10.

FIG. 12 is a partial sectional view taken along the line 12-12 in FIG. 11.

FIG. 13 is a perspective view of that portion of the mast carrying the horseshoe-shaped member and the first stay.

FIG. 14 is a view looking down on the mast, horseshoe-shaped member and first stay of FIG. 13.

FIG. 15 is a rear view of the mast, horseshoe-shaped member and first stay of FIG. 13.

FIG. 16 is a side view of the mast, horseshoe-shaped member and first stay of FIG. 13.

FIG. 17 is a top view of the mast showing the sail as it is being furled around the mast as the mast is rotated.

DESCRIPTION OF THE PREFERRED EMBODIMENTS

Turning to the drawings in more detail, the watercraft 10 has a vertical mast 12 which is rotatable about its own vertical axis and is retained in a suitable fitting within the structure of the watercraft. The mast 12 carries sail 14.

The first member preferably is generally a horseshoe-shaped member 16 having an open end or gap 18 and otherwise extends around the mast. The horseshoe-shaped member 16 is supported by a stay 20 running from horseshoe-shaped member 16 to a second member which is bearing mounted member 22 carried by the top 24 of the mast 12. The bearings are shown in FIG. 10 at 26.

The mast 12 is freely rotatable within the horseshoe-shaped member 16 and also with respect to the bearing mounted member 22.

Additional stays 28 and 30 extend from the horseshoe-shaped member 16 to the sides of the watercraft at 32 and 34, respectively.

In furling, the sail 14 passes through the gap 18 between guide rollers 36 located at each side the open end 18 of horseshoe-shaped member 16. As the mast is rotated, the sail 12 is snugly furled around the mast 12, as show in FIG. 17.

When the sail 12 is unfurled, the free end is held by stay 38 attached to cross-member 40.

The sail 14 has a sleeve 42 or pocket along the length of its front end. When assembled with the mast 12, the mast is inserted into sleeve 42 and then the sail is affixed top and bottom to the mast. In this way when the sail is furled, it starts to wind around the mast as the mast is rotated.

The watercraft shown is a catamaran. However, the invention is applicable to sail boats generally, as will be apparent to those skilled in the art.

The invention claimed is:

1. A wind powered craft comprising a generally vertical mast which is rotatable about its vertical axis;
   a sail carried by said mast with its bottom edge attached in proximity to the bottom of the mast and extending to an attachment point in proximity to the top of the mast;
   a first member having an open end and partially extending around said mast, the mast being rotatable within said member;
   a bearing mounted stationary second member at the top of the mast and carried by the mast while allowing the mast to rotate;
   at least one support stay running from said first member to said bearing mounted second member to support said first member;
   said sail being adapted to be reefed by furling completely around said mast by passing freely through the open end of said first member upon rotation of the mast.

2. A wind powered craft comprising a generally vertical mast which is rotatable about its vertical axis;
   a sail carried by said mast with its bottom edge attached in proximity to the bottom of the mast and extending to an attachment point in proximity to the top of the mast;
   a first member having an open end and partially extending around said mast, the mast being rotatable within said member;
   a bearing mounted stationary second member at the top of the mast and carried by the mast while allowing the mast to rotate;
   at least one support stay running from said first member to said bearing mounted second member to support said first member;
   additional stays attached to said first member and splayed to attach to opposed sides of the hull of the watercraft, said sail being reefed around said mast through the open end of said first member by rotation of the mast;
   said sail being adapted to be reefed by furling completely around said mast by passing freely through the open end of said first member upon rotation of the mast.

3. A watercraft comprising a generally vertical mast which is rotatable about its vertical axis;
   a sail carried by said mast with its bottom edge attached in proximity to the bottom of the mast and extending to an attachment point in proximity to the top of the mast;
   a generally horseshoe-shaped member having an open end and partially extending around said mast, the mast being rotatable within the horseshoe-shaped member;
   a bearing mounted stationary member at the top of the mast and carried by the mast while allowing the mast to rotate;
   at least one support stay running from said horseshoe-shaped member to said bearing mounted member to support the horseshoe-shaped member;
   said sail being adapted to be reefed by furling completely around said mast by passing freely through the open end of said generally horseshoe-shaped member upon rotation of the mast.

4. The craft of claim 1 or 2 wherein the open end of said first member has opposed rollers for contacting and guiding the sail as it is reefed around the mast.

5. The craft of claim 1 or 2 wherein the first member is positioned approximately two-thirds to three-quarters up the length of the mast.

6. The craft of claim 1 or 2 or 3 wherein the craft is a catamaran.

\* \* \* \* \*